US012630503B2

(12) United States Patent
Lee

(10) Patent No.: US 12,630,503 B2
(45) Date of Patent: May 19, 2026

(54) METHOD FOR PRODUCING BENZOPYRANONE COMPOUND AND NOVEL INTERMEDIATE USED THEREIN

(71) Applicant: ILAb, Bucheon-si (KR)

(72) Inventor: Suk Ho Lee, Hwaseong-si (KR)

(73) Assignee: ILAb, Bucheon-si (KR)

( * ) Notice: Subject to any disclaimer, the term of this patent is extended or adjusted under 35 U.S.C. 154(b) by 788 days.

(21) Appl. No.: 17/919,660

(22) PCT Filed: Mar. 17, 2021

(86) PCT No.: PCT/KR2021/095035

§ 371 (c)(1),
(2) Date: Oct. 18, 2022

(87) PCT Pub. No.: WO2021/215900

PCT Pub. Date: Oct. 28, 2021

(65) Prior Publication Data

US 2023/0150928 A1 May 18, 2023

(30) Foreign Application Priority Data

Apr. 20, 2020 (KR) ........................ 10-2020-0047341

(51) Int. Cl.
*C07D 311/30* (2006.01)
*A61K 31/352* (2006.01)
*C07C 65/24* (2006.01)
*C07C 311/30* (2006.01)

(52) U.S. Cl.
CPC .......... *C07C 311/30* (2013.01); *A61K 31/352* (2013.01); *C07C 65/24* (2013.01); *C07B 2200/13* (2013.01)

(58) Field of Classification Search
CPC ....... C07C 311/30; C07C 65/24; C07C 69/76; A61K 31/352; C07B 2200/13; A61P 19/02; A61P 29/00; A61P 1/00; C07D 311/30
USPC .......................................................... 549/402
See application file for complete search history.

(56) References Cited

U.S. PATENT DOCUMENTS

2007/0123511 A1 5/2007 Sakata et al.

FOREIGN PATENT DOCUMENTS

| | | | | |
|---|---|---|---|---|
| CA | 3074993 A1 * | 4/2019 | | A23L 33/10 |
| CN | 108676063 A | 10/2018 | | |
| KR | 10-2008-0013162 A | 2/2008 | | |
| KR | 10-1934651 B1 | 1/2019 | | |
| KR | 10-2019-0044025 A | 4/2019 | | |
| KR | 10-2021-0026308 A | 3/2021 | | |

OTHER PUBLICATIONS

Wikipedia, Solvent Sep. 6, 2018, p. 1-15 (Year: 2018).*
International Search Report of PCT/KR2021/095035 dated Aug. 3, 2021 [PCT/ISA/210].

* cited by examiner

*Primary Examiner* — Taylor V Oh
(74) *Attorney, Agent, or Firm* — Sughrue Mion, PLLC

(57) ABSTRACT

The present invention relates to a method for preparing 2-(2,5-difluorophenyl)-3-carboxy-7-chloro-(4H)-4-benzopyranone represented by formula 1 below, a novel intermediate used therein, and a method for preparing the same. Specifically, an object of the present invention is to provide a novel preparation method, in which the compound of formula 1 below can be efficiently and economically synthesized and can be mass-produced in a high yield.

[Formula 1]

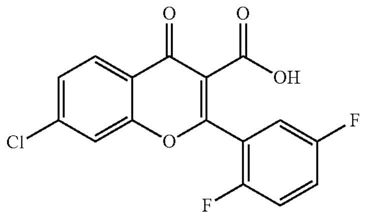

16 Claims, No Drawings

METHOD FOR PRODUCING BENZOPYRANONE COMPOUND AND NOVEL INTERMEDIATE USED THEREIN

CROSS REFERENCE TO RELATED APPLICATIONS

This application is a National Stage of International Application No. PCT/KR2021/095035, filed Mar. 17, 2021, claiming priority to Korean Patent Application No. 10-2020-0047341, filed Apr. 20, 2020, the entire disclosures of which are incorporated herein by reference.

TECHNICAL FIELD

The present invention relates to a method for preparing 2-(2,5-difluorophenyl)-3-carboxy-7-chloro-(4H)-4-benzopyranone represented by formula 1 below and a novel intermediate used therein.

[Formula 1]

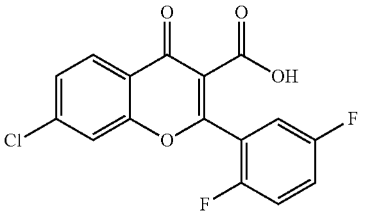

BACKGROUND ART

TNF is a type of cytokine and normal TNF plays an important role in an inflammatory response, but excessively produced TNF stimulates macrophages and induces an excessive inflammatory response in the cells, leading to various TNF related diseases such as rheumatoid arthritis, inflammatory bowel disease, psoriasis, ankylosing spondylitis, and the like. Examples of TNF inhibitors for treating TNF related diseases include etanercept, adalimumab, infliximab, and the like. These are biopharmaceuticals, which have disadvantages that they are expensive, require repeated injections, have the potential to develop resistance, and are difficult to store.

Korean Patent Registration No. 10-1934651 discloses that 2-(2,5-difluorophenyl)-3-carboxy-7-chloro-(4H)-4-benzopyranone, which is a compound having the structure of formula 1 below (hereinafter, "compound of formula 1"), as a novel compound that directly binds to TNF and inhibits TNF activity. This compound has an excellent inhibitory effect of cytotoxicity of TNF and an inhibitory effect of cell binding of TNF, inhibits cell signal transduction by TNF, exhibits therapeutic effects on sepsis, rheumatoid arthritis, inflammatory bowel disease, sepsis-induced acute kidney injury, and the like, and exhibits comparable effects even when compared to commercially available adalimumab and etanercept.

[Formula 1]

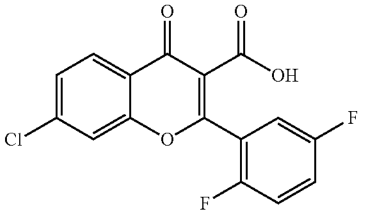

Korean Patent Registration No. 10-1934651 discloses a preparation method as follows. According to this, when $R^3$, $R^4$ and $R^6$ are hydrogen and $R^5$ is Cl, the compound of formula 1 can be prepared through a total of 3 steps.

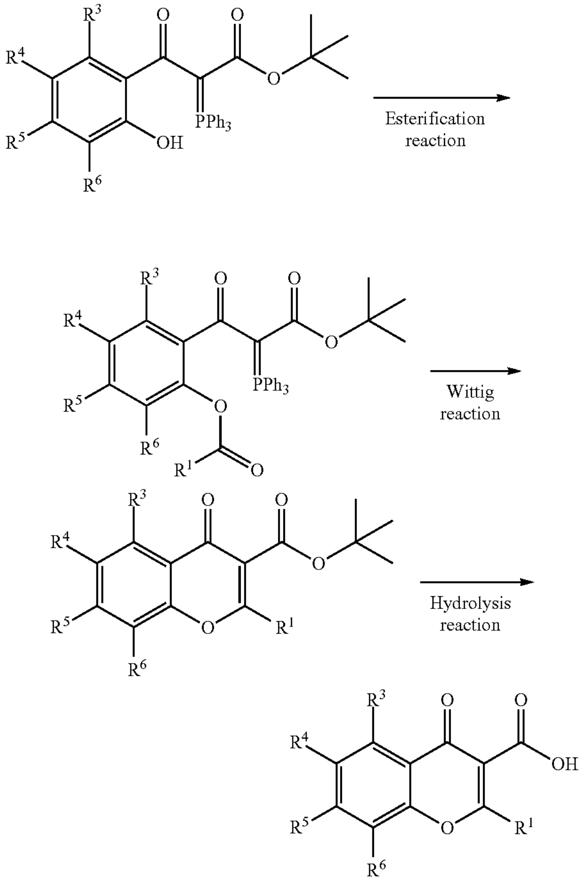

However, several additional steps are required to synthesize the starting material of the disclosed preparation method, and specifically, it can be synthesized from 4-chloro-2-hydroxybenzoic acid through the following four additional steps.

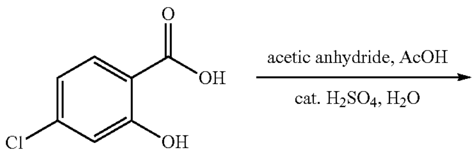

-continued

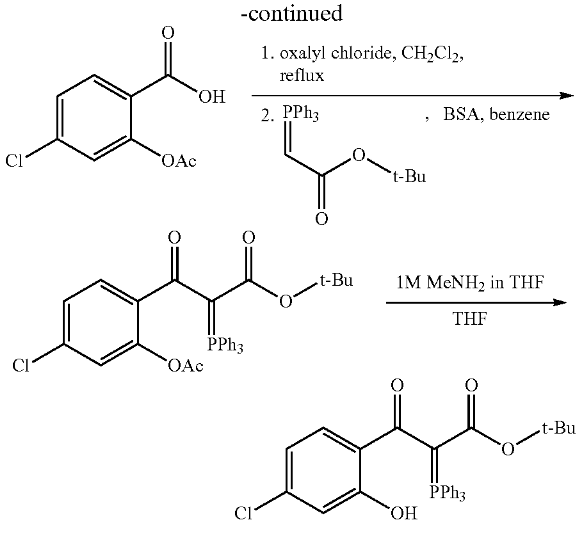

That is, a total of 7 steps are required to prepare the compound of formula 1 using 4-chloro-2-hydroxybenzoic acid as a starting material.

In the preparation method, for the synthesis of the compound of formula 1, a phosphorane group is first introduced into 4-chloro-2-hydroxybenzoic acid, and then a 2,5-difluorobenzoyloxy group is introduced, and then a 4-benzopyranone compound is synthesized through a Wittig reaction, According to this, the reaction step of introducing a phosphorane group and the Wittig reaction are divided into separate steps to increase the number of the reaction steps, and in order to introduce a phosphorane group first, the reaction of attaching a protecting group of a hydroxy group and a deprotection reaction are additionally performed to increase the number of the reaction steps. In addition, the preparation method has a problem that the yield is very low, less than 15%, and thus not suitable for mass synthesis.

Therefore, there is a need for a more efficient and economical preparation method to commercially produce the compound of formula 1.

Accordingly, the present inventors developed a novel preparation method, in which the compound of formula 1 can be efficiently and economically synthesized and can be mass-produced in a high yield. Based on the above, the present inventors completed the present invention.

PRIOR ART DOCUMENT

Patent Document (Patent Document 1) Korean Patent Registration No. 10-1934651

DETAILED DESCRIPTION OF THE INVENTION

Technical Problem

An object of the present invention is to provide a novel method for preparing a compound of formula 1 below, in which the compound of formula 1 below can be efficiently and economically synthesized and can be mass-produced in a high yield.

[Formula 1]

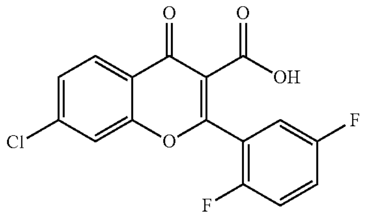

In addition, another object of the present invention is to provide compounds of formulas 2 and 3 below, which are novel intermediates used in a method for preparing a compound of formula 1.

[Formula 2]

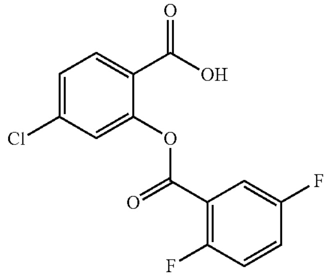

[Formula 3]

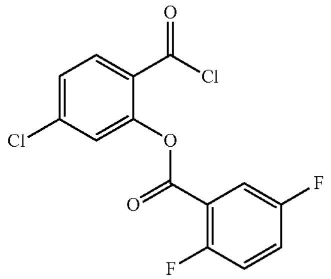

In addition, another object of the present invention is to provide a method for preparing compounds of formulas 2 and 3.

Solution to Problem

The present invention provides novel compounds of formulas 2 and 3 below.

[Formula 2]

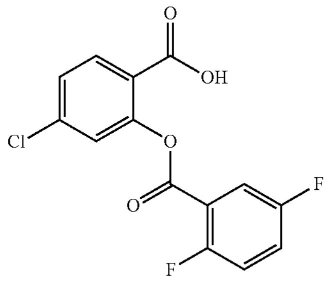

-continued

[Formula 3]

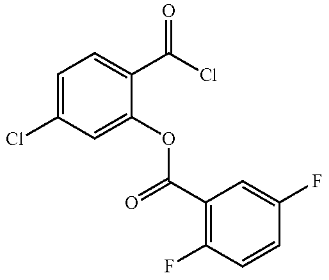

The present invention provides a method for preparing the compound of formula 2.

In one embodiment, the compound of formula 2 may be prepared by reacting 4-chloro-2-hydroxybenzoic acid with 2,5-difluorobenzoyl chloride. The reaction may be carried out at −20 to 0° C. in at least one reaction solvent selected from the group consisting of tetrahydrofuran (THF), ether, methyl tert-butyl ether (MTBE), dichloromethane (DCM), acetonitrile (ACN), ethyl ether, and dioxin in the presence of at least one base selected from the group consisting of pyridine, triethylamine (TEA), diisopropylethylamine (DIPEA), dimethylaminopyridine (DMAP), potassium hydroxide, potassium carbonate, sodium acetate, lutidine, sodium carbonate, sodium hydrogen carbonate, potassium hydrogen carbonate, and cesium carbonate, but is not limited thereto.

The present invention provides a method for preparing the compound of formula 3.

In one embodiment, the compound of formula 3 may be prepared by reacting the compound of formula 2 with oxalyl chloride. The reaction may be carried out at room temperature in at least one reaction solvent selected from the group consisting of dichloromethane (DCM) and dimethylformamide (DMF), but is not limited thereto.

The present invention provides a method for preparing a compound of formula 1 below.

[Formula 1]

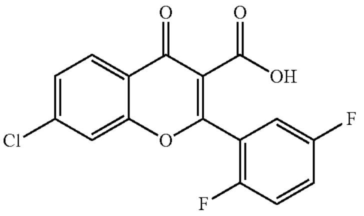

The compound of formula 1 may be prepared by a preparation method comprising the steps of reacting the compound of formula 3 with a compound of formula 4 below to obtain a compound of formula 5 below; and treating a compound of formula 5 below with an acid to obtain the compound of formula 1.

[Formula 4]

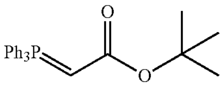

-continued

[Formula 5]

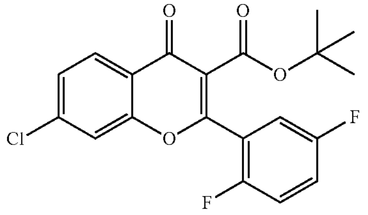

In addition, by adjusting the pH of the reaction mixture obtained after reacting the compound of formula 3 with the compound of formula 4 to pH 7 or less, the generation of impurities may be reduced. The step of obtaining the compound of formula 5 may be carried out in at least one reaction solvent selected from the group consisting of toluene, tetrahydrofuran (THF), and dichloromethane (DCM) in the presence of at least one base selected from the group consisting of N,O-bis(trimethylsilyl) acetamide, triethylamine (TEA), and diisopropylethylamine (DIPEA), but is not limited thereto. The step of obtaining the compound of formula 1 may be carried out in at least one reaction solvent selected from the group consisting of ethyl acetate (EA), methanol, isopropyl alcohol (i-PrOH), and methyl tert-butyl ether (MTBE), and the acid may be hydrochloric acid or trifluoroacetic acid, but is not limited thereto.

In another embodiment, the compound of formula 1 may be prepared by a preparation method comprising the steps of reacting the compound of formula 2 with oxalyl chloride to obtain the compound of formula 3; reacting the compound of formula 3 with the compound of formula 4 to obtain the compound of formula 5; and treating the compound of formula 5 with an acid to obtain the compound of formula 1.

The step of obtaining the compound of formula 3 may be carried out at room temperature in at least one reaction solvent selected from the group consisting of dichloromethane (DCM) and dimethylformamide (DMF), but is not limited thereto.

Here, whether the compound of formula 3 is prepared and yield may be confirmed by confirming whether a compound of formula 6 below is prepared by reacting the compound of formula 2 with oxalyl chloride, and then reacting the prepared compound of formula 3 with methanol. The steps of confirming whether the compound of formula 3, which is difficult to be separated, is obtained by confirming whether a compound of formula 6 below is obtained, and then reacting the compound of formula 3 with the compound of formula 4 to obtain the compound of formula 5 may be carried out.

[Formula 6]

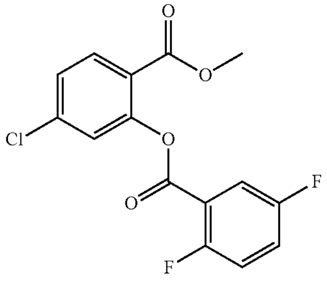

In another embodiment, the compound of formula 1 may be prepared by a preparation method comprising the steps of reacting 4-chloro-2-hydroxybenzoic acid with 2,5-difluorobenzoyl chloride to obtain the compound of formula 2; reacting the compound of formula 2 with oxalyl chloride to obtain the compound of formula 3; reacting the compound of formula 3 with the compound of formula 4 to obtain the compound of formula 5; treating the compound of formula 5 with an acid to obtain the compound of formula 1.

The step of obtaining the compound of formula 2 may be carried out at −20 to 0° C. in at least one reaction solvent selected from the group consisting of tetrahydrofuran (THF), ether, methyl tert-butyl ether (MTBE), dichloromethane (DCM), acetonitrile (ACN), ethyl ether, and dioxin in the presence of at least one base selected from the group consisting of pyridine, triethylamine (TEA), diisopropylethylamine (DIPEA), dimethylaminopyridine (DMAP), potassium hydroxide, potassium carbonate, sodium acetate, lutidine, sodium carbonate, sodium hydrogen carbonate, potassium hydrogen carbonate, and cesium carbonate, but is not limited thereto.

In one embodiment, the compound of formula 1 may be prepared according to Reaction Scheme 1 below.

[Reaction Scheme 1]

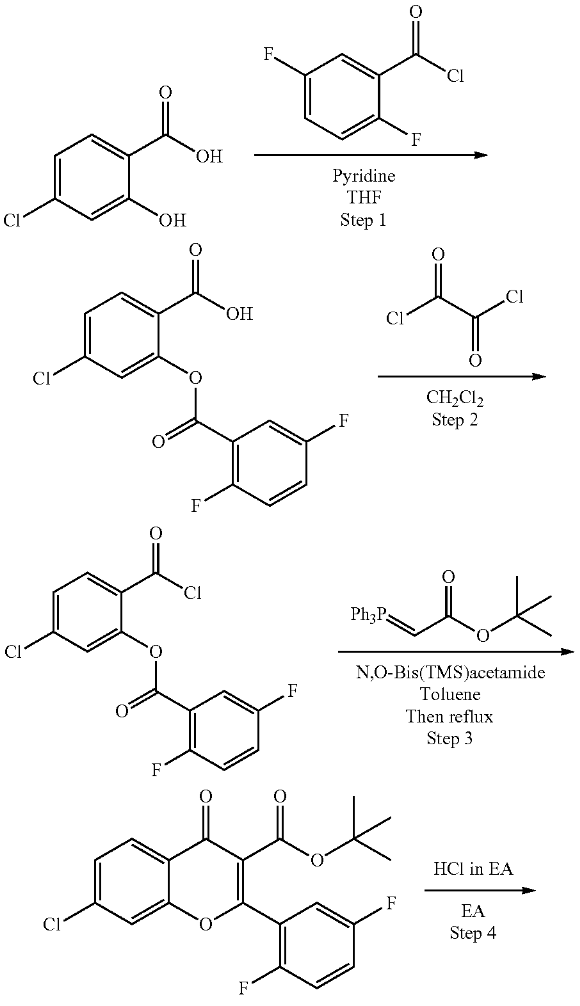

-continued

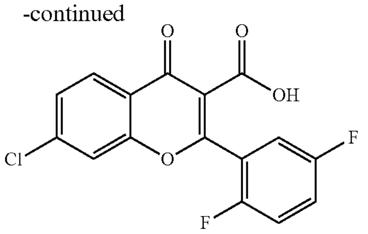

The present invention provides a method for preparing a form IV crystal of the compound of formula 1.

In one embodiment, a form IV crystal of the compound of formula 1 may be prepared by adding the compound of formula 1 to methyl isobutyl ketone (MIBK). The temperature at which the compound of formula 1 is added to the methyl isobutyl ketone (MIBK) may be 15 to 25° C.

In one embodiment, a form IV crystal of the compound of formula 1 may be prepared by preparing the compound of formula 1 by the method for preparing a compound of formula 1 according to the present invention, and then adding the compound of formula 1 to methyl isobutyl ketone (MIBK).

In one embodiment, a form IV crystal of the compound of formula 1 may be prepared by a method comprising the steps of reacting 4-chloro-2-hydroxybenzoic acid with 2,5-difluorobenzoyl chloride to obtain the compound of formula 2; reacting the compound of formula 2 with oxalyl chloride to obtain the compound of formula 3; reacting the compound of formula 3 with the compound of formula 4 to obtain the compound of formula 5; treating the compound of formula 5 with an acid to obtain the compound of formula 1; and adding the compound of formula 1 to methyl isobutyl ketone (MIBK) to obtain a form IV crystal of the compound of formula 1.

The form IV crystal of the compound of formula 1 may exhibit an X-ray powder diffraction (XRPD) spectrum comprising characteristic peaks at four or more diffraction angles $2\theta \pm 0.2°$ selected from the group consisting of 11.3, 14.7, 14.9, 16.9, 17.2, 22.5, and 25.7. The form IV crystal may have an endothermic peak in the range of about 160° C. to about 170° C. in differential scanning calorimetry (DSC) analysis under an elevated temperature condition of 10° C./min, or may have no weight loss at 160° C. or lower in a thermogravimetric (TGA) curve.

The present invention provides the compound of formula 1 prepared by the method for preparing a compound of formula 1 according to the present invention.

The present invention provides a composition for treating or preventing a TNF overexpression disease selected from the group consisting of rheumatoid arthritis, juvenile rheumatoid arthritis, inflammatory bowel disease, Crohn's disease, ulcerative colitis, psoriasis, plaque psoriasis, plaque psoriasis in children, psoriatic arthritis, polyarticular juvenile idiopathic arthritis, Behcet's enteritis, ankylosing spondylitis, axial spondyloarthritis, juvenile enthesitis related arthritis, osteoarthritis, polymyalgia rheumatica, multiple sclerosis, systemic lupus erythematosus, asthma, Sjogren's syndrome, pneumonia, chronic obstructive pulmonary disease, sarcoidosis, granuloma annulare, Wegener's granulomatosis, arteriosclerosis, vasculitis, heart failure, myocardial infarction, kidney injury, nephritis, graft-versus-host disease, dementia, Alzheimer's disease, Parkinson's disease, pain, uveitis, Behcet's disease, hidradenitis suppurativa, pityriasis rubra pilaris, necrobiosis lipoidica diabeticorum, pyoderma gangrenosum, Sweet's syndrome, subcorneal pustular dermatosis, scleroderma, dermatomyositis, sepsis and septic shock, the composition comprising the compound of formula 1 prepared by the method for preparing a compound of formula 1 according to the present invention.

Effects of the Invention

The preparation method of the present invention reduces the number of the preparation steps compared to a conventional preparation method by carrying out the synthesis of a phosphorane intermediate compound and the synthesis of a 4-benzopyranone compound through Wittig reaction in one step in the steps of introducing 2,5-difluorobenzoyloxy group into 4-chloro-2-hydroxy benzoic acid, and then reacting tert-butyl 2-(triphenylphosphoranylidene) acetate represented by formula 4 for the synthesis of the compound of formula 1.

In addition, the present invention enhanced the yield of the compound of formula 1 by separating the compound of formula 3, which is a reaction intermediate compound, so that the yield of the intermediate compound and whether the reaction proceeds can be confirmed.

In addition, the present invention further enhanced the yield by reducing the generation of impurities by adjusting the pH of the reaction mixture obtained after reacting the compound of formula 3 with the compound of formula 4.

Therefore, the present invention can synthesize the compound of formula 1 economically and efficiently by omitting unnecessary steps in a conventional preparation method and reducing the reaction rate and can obtain the compound of formula 1 in a higher yield through intermediate separation and pH adjustment.

Accordingly, the compound of formula 1 can be commercially mass-produced through the method for preparing a compound of formula 1 of the present invention.

BEST MODE FOR CARRYING OUT THE INVENTION

Hereinafter, the present invention will be described in more detail through the following examples, but the following examples are for illustrative purposes only and are not intended to limit the scope of the present invention.

[Example 1] Preparation of 4-chloro-2-((2,5-difluorobenzoyl)oxy)benzoic acid

[Reaction Scheme 2]

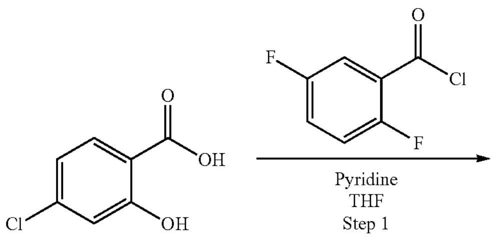

-continued

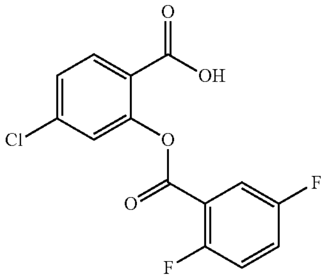

Tetrahydrofuran (THF) (15 L), 4-chloro-2-hydroxybenzoic acid (3.9 kg), pyridine (1.79 kg) were placed in a reactor at 15~30° C. and cooled to −20~0° C. while stirring. In a separate apparatus, a solution of tetrahydrofuran (THF) (45 L) and 2,5-difluorobenzoyl chloride (3.99 kg) was prepared and then slowly added dropwise to the mixture. After the reaction was completed, ethyl acetate (EA) was added to the reaction product at −10~0° C. After the reaction was terminated by adding purified water, the reaction temperature was elevated to room temperature. Ethyl acetate (EA) (20 L) was added and then washed with water (20 L), and then the aqueous layer was removed. The organic layer was washed with 1 M HCl (9 L). The organic layer was washed with water (9 L) until the pH reached pH 4~5. The organic layer was concentrated under reduced pressure and then dissolved in dimethylformamide (DMF) (18 L), and water (72 L) was added and then stirred for 6 hours at room temperature. The resulting solid was filtered and then washed twice with water (9 L), and the solid was dried under vacuum at 40~50° C. for 17 hours to obtain 6.4 kg of 4-chloro-2-((2,5-difluorobenzoyl)oxy)benzoic acid (purity: 99%, yield: 89.5%).

When diisopropylethylamine (DIPEA), potassium hydroxide (KOH), potassium carbonate ($K_2CO_3$) or sodium acetate ($CH_3COONa$) was used instead of pyridine in the above reaction, 4-chloro-2-((2,5-difluorobenzoyl)oxy)benzoic acid with a purity of 73.1%, 52.4%, 39.0% or 55.4% was obtained.

When the above reaction was carried out in ether, methyl tert-butyl ether (MTBE) or dichloromethane (DCM) instead of tetrahydrofuran (THF), 4-chloro-2-((2,5-difluorobenzoyl)oxy)benzoic acid with a purity of 77.1%, 54.6% or 47.4% was obtained.

When the above reaction was carried out in acetonitrile (ACN) using diisopropylethylamine (DIPEA), 4-chloro-2-((2,5-difluorobenzoyl)oxy)benzoic acid with a purity of 61.1% was obtained. When the above reaction was carried out in dichloromethane (DCM) using triethylamine (TEA), 4-chloro-2-((2,5-difluorobenzoyl)oxy)benzoic acid with a purity of 37.5% was obtained. When the above reaction was carried out in methyl tert-butyl ether (MTBE) using triethylamine (TEA), 4-chloro-2-((2,5-difluorobenzoyl)oxy)benzoic acid with a purity of 58.3% was obtained. When the above reaction was carried out in dichloromethane (DCM) using triethylamine (TEA) and dimethylaminopyridine (DMAP) together, 4-chloro-2-((2,5-difluorobenzoyl)oxy)benzoic acid with a purity of 41.8% was obtained.

[Example 2] Preparation of 5-chloro-2-(chlorocarbonyl)phenyl 2,5-difluorobenzoate

[Reaction Scheme 3]

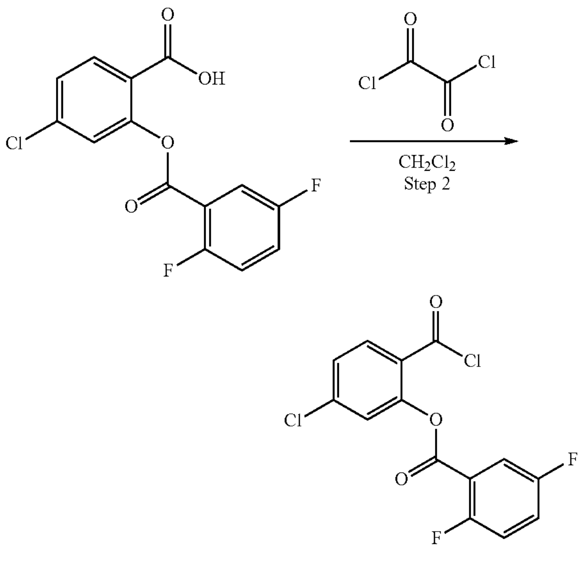

Dichloromethane (DCM) (35 L) and 4-chloro-2-((2,5-difluorobenzoyl)oxy)benzoic acid (6.2 kg) was added to a reactor, and then dimethylformamide (DMF) (10 mL) was added to a reactor. Oxalyl chloride (5.0 kg) was slowly added dropwise at room temperature while stirring and then stirred for additional 3 hours. The mixture was concentrated under reduced pressure, and n-heptane (35 L) was added and stirred for 2 hours at 40° C. or lower. After concentration of n-heptane until the volume reached about 50~60 L, the reaction solution was cooled to room temperature and further stirred for additional 1~2 hours. The resulting solid was filtered, washed with n-heptane (9 L), and then dried under vacuum at 30~40° C. for 30 hours to obtain 5.84 kg of 5-chloro-2-(chlorocarbonyl) phenyl 2,5-difluorobenzoate (purity: 100%, yield: 88.2%).

[Example 3] Preparation of tert-butyl 7-chloro-2-(2,5-difluorophenyl)-4-oxo-4H-chromene-3-carboxylate

[Reaction Scheme 4]

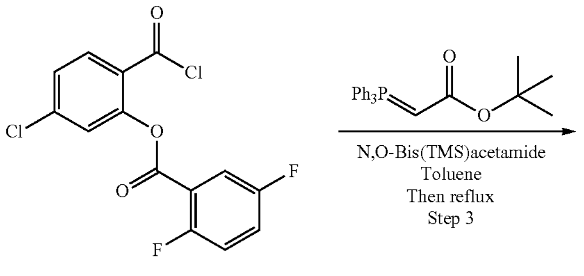

-continued

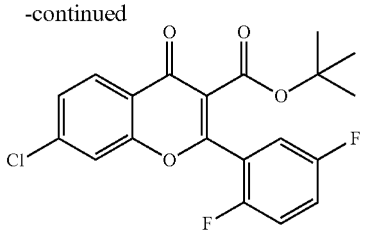

Step 1:

Toluene (36 L), tert-butyl 2-(triphenylphosphoranylidene) acetate (7.78 kg) and N,O-bis(trimethylsilyl) acetamide (7.01 kg) were added to a reactor at room temperature. The reaction solution was cooled to −5~5° C. while stirring, and then 5-chloro-2-(chlorocarbonyl) phenyl 2,5-difluorobenzoate (5.7 kg) was slowly added to a reactor and then stirred for 22 hours. After the reaction was terminated using a 5% aqueous sodium hydrogen carbonate solution, dichloromethane (DCM) was added, and the temperature of the reaction solution was elevated to 25~35° C. The reaction mixture was washed with water (10 L) until the pH of the aqueous phase reached pH 7 or less.

Step 2:

The organic layer was stirred under reflux at 95~105° C. Thereafter, the reaction mixture was cooled to 50~60° C. and concentrated, and then the residue was slurried in isopropyl alcohol (IPA) (15 L) until the toluene residue reached 1.0% or less. The temperature of the mixture was adjusted to 17~23° C., and then for crystallization, the mixture was stirred at 17~23° C. until the weight of tert-butyl 7-chloro-2-(2,5-difluorophenyl)-4-oxo-4H-chromene-3-carboxylate in the mother liquid reached 2.0 wt % or less. The suspension was filtered, and the solid was washed with isopropyl alcohol (3 L), and then the solid was dried under vacuum at 30~40° C. for 17 hours until the total content of isopropyl alcohol (IPA) and toluene reached 1.0 wt % or less. Thereafter, the temperature was cooled to 20~30° C. to obtain 4.46 kg of tert-butyl 7-chloro-2-(2,5-difluorophenyl)-4-oxo-4H-chromene-3-carboxylate (purity: 99.8%, yield: 65.4%).

When triethylamine (TEA) or diisopropylethylamine (DIPEA) was used instead of N,O-bis(trimethylsilyl) acetamide in the above reaction, tert-butyl 7-chloro-2-(2,5-difluorophenyl)-4-oxo-4H-chromene-3-carboxylate with a purity of 76.0% or 70.0% was obtained.

When the above reaction was carried out in tetrahydrofuran (THF) or dichloromethane (DCM) instead of toluene, tert-butyl 7-chloro-2-(2,5-difluorophenyl)-4-oxo-4H-chromene-3-carboxylate with a purity of 56.1% or 21.7% was obtained.

[Example 4] Preparation of 2-(2,5-difluorophenyl)-3-carboxy-7-chloro-(4H)-4-benzopyranone

[Reaction Scheme 5]

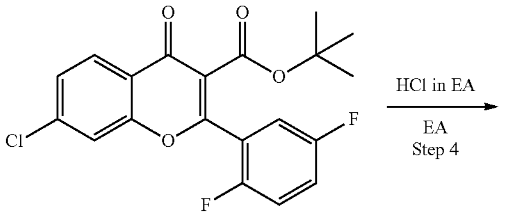

-continued

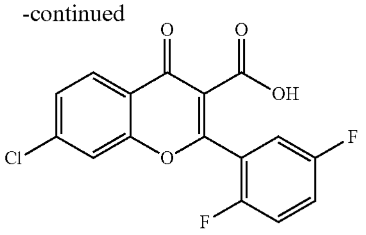

Ethyl acetate (EA) (12.6 L) and tert-butyl 7-chloro-2-(2,5-difluorophenyl)-4-oxo-4H-chromene-3-carboxylate (4.2 kg) were added to a reactor, and then completely dissolved at 45~55° C., and then cooled to 15~25° C. A 4 M HCl/ethyl acetate (EA) (21.0 L) solution was slowly added dropwise to the reaction solution and then stirred for 42 hours. The resulting solid was washed with n-heptane (22.5 L) and water (22.5 L), respectively. It was dried under vacuum at 40~50° C. for 27 hours.

8.2 kg of methyl isobutyl ketone (MIBK) was added to a reactor, and 2-(2,5-difluorophenyl)-3-carboxy-7-chloro-(4H)-4-benzopyranone was added. The mixture was stirred at 15~25° C. for 23 hours until the crystalline form of 2-(2,5-difluorophenyl)-3-carboxy-7-chloro-(4H)-4-benzopyranone became form IV. The solid was filtered, washed with methyl tert-butyl ether (MTBE), and then dried under vacuum at 30~40° C. for 26 hours to obtain 2.75 kg of 2-(2,5-difluorophenyl)-3-carboxy-7-chloro-(4H)-4-benzopyranone (purity: 99.9%, yield: 75.4%).

When the above reaction was carried out in methanol, isopropyl alcohol (i-PrOH) or methyl tert-butyl ether (MTBE) instead of ethyl acetate (EA), 2-(2,5-difluorophenyl)-3-carboxy-7-chloro-(4H)-4-benzopyranone with a purity of 52.2%, 28.3% or 85.8% was obtained.

The invention claimed is:

1. A compound of formula 2 below:

[Formula 2]

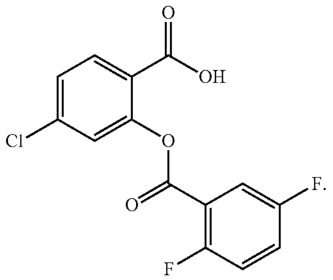

2. A compound of formula 3 below:

[Formula 3]

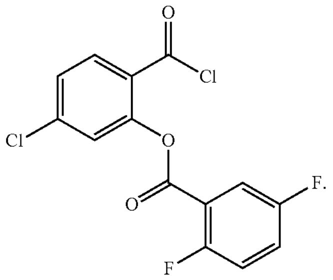

3. A method for preparing the compound of formula 2 according to claim 1, comprising reacting 4-chloro-2-hydroxybenzoic acid with 2,5-difluorobenzoyl chloride to obtain the compound of formula 2

[Formula 2]

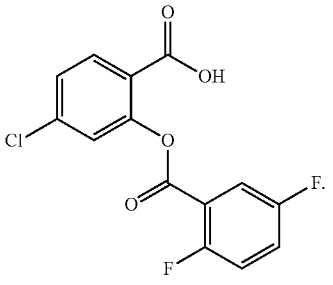

4. The method according to claim 3, wherein a reaction is carried out at −20 to 0° C. in at least one reaction solvent selected from the group consisting of tetrahydrofuran (THF), ether, methyl tert-butyl ether (MTBE), dichloromethane (DCM), acetonitrile (ACN), ethyl ether, and dioxin in the presence of at least one base selected from the group consisting of pyridine, triethylamine (TEA), diisopropylethylamine (DIPEA), dimethylaminopyridine (DMAP), potassium hydroxide, potassium carbonate, sodium acetate, lutidine, sodium carbonate, sodium hydrogen carbonate, potassium hydrogen carbonate, and cesium carbonate.

5. The method for preparing the compound of formula 3 according to claim 2, comprising reacting a compound of formula 2 below with oxalyl chloride to obtain the compound of formula 3

[Formula 2]

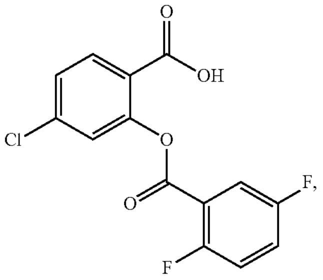

[Formula 3]

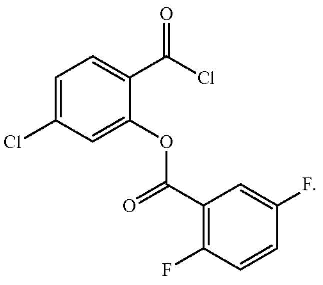

6. The method according to claim 5, wherein a reaction is carried out at room temperature in at least one reaction solvent selected from the group consisting of dichloromethane (DCM) and dimethylformamide (DMF).

7. A method for preparing a compound of formula 1, comprising (i) reacting the compound of formula 3 of claim 2 with a compound of formula 4 below to obtain a compound of formula 5 below; and (ii) treating a compound of formula 5 below with an acid to obtain the compound of formula 1 below

[Formula 1]

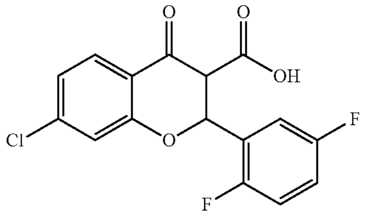

[Formula 3]

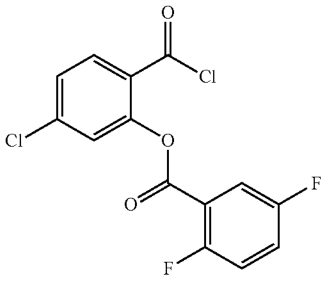

[Formula 4]

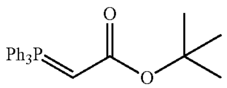

[Formula 5]

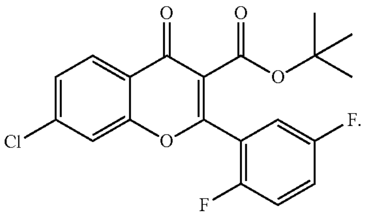

8. The method according to claim 7, wherein in step (i), the reaction mixture obtained after reacting the compound of formula 3 with the compound of formula 4 is adjusted to pH 7 or less.

9. The method according to claim 7, wherein step (i) is carried out in at least one reaction solvent selected from the group consisting of toluene, tetrahydrofuran (THF), and dichloromethane (DCM) in the presence of at least one base selected from the group consisting of N,O-bis(trimethylsilyl) acetamide, triethylamine (TEA), and diisopropylethylamine (DIPEA).

10. The method according to claim 7, wherein step (ii) is carried out in at least one reaction solvent selected from the group consisting of ethyl acetate (EA), methanol, isopropyl alcohol (i-PrOH), and methyl tert-butyl ether (MTBE), and the acid is hydrochloric acid or trifluoroacetic acid.

11. The method according to claim 7, further comprising reacting a compound of formula 2 below with oxalyl chloride to obtain the compound of formula 3

[Formula 2]

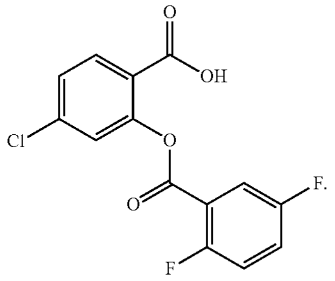

12. The method according to claim 11, further comprising reacting 4-chloro-2-hydroxybenzoic acid with 2,5-difluorobenzoyl chloride to obtain the compound of formula 2.

13. A method for preparing a compound of formula 1, comprising reacting 4-chloro-2-hydroxybenzoic acid with 2,5-difluorobenzoyl chloride to obtain a compound of formula 2 below;

reacting the compound of formula 2 of claim 1 with oxalyl chloride to obtain a compound of formula 3 below;

reacting a compound of formula 3 below with a compound of formula 4 below to obtain a compound of formula 5 below; and treating a compound of formula 5 below with an acid to obtain a compound of formula 1 below.

[Formula 1]

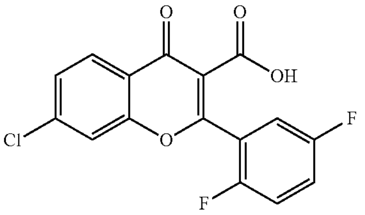

[Formula 2]

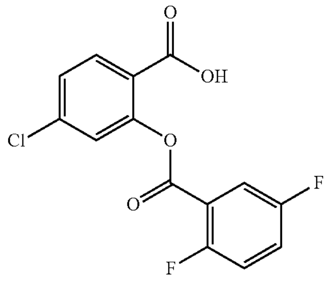

[Formula 3]

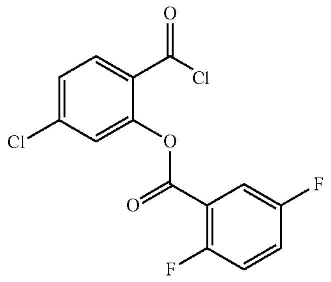

[Formula 4]

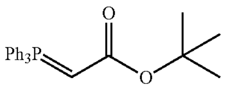

-continued

[Formula 5]

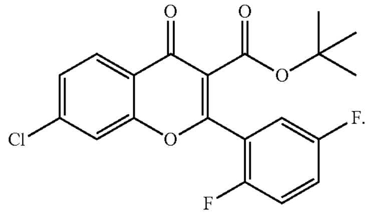

14. A method for preparing a form IV crystal of a compound of formula 1, comprising adding the compound of formula 1 below to methyl isobutyl ketone (MIBK) to obtain the form IV crystal of the compound of formula 1

[Formula 1]

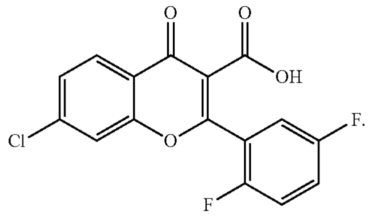

wherein the form IV crystal exhibits characteristic peaks at four or more diffraction angles 2θ±0.2° selected from the group consisting of 11.3, 14.7, 14.9, 16.9, 17.2, 22.5, and 25.7.

15. A method for preparing a form IV crystal of a compound of formula 1, comprising reacting 4-chloro-2-hydroxybenzoic acid with 2,5-difluorobenzoyl chloride to obtain the compound of formula 2 of claim 1;

reacting a compound of formula 2 below with oxalyl chloride to obtain a compound of formula 3 below;

reacting a compound of formula 3 below with a compound of formula 4 below to obtain a compound of formula 5 below;

treating a compound of formula 5 below with an acid to obtain a compound of formula 1 below; and adding a compound of formula 1 below to methyl isobutyl ketone (MIBK) to obtain a form IV crystal of a compound of formula 1

[Formula 1]

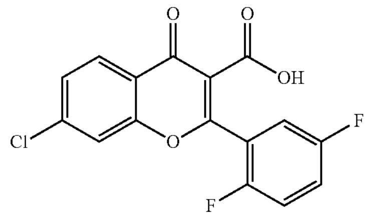

-continued

[Formula 2]

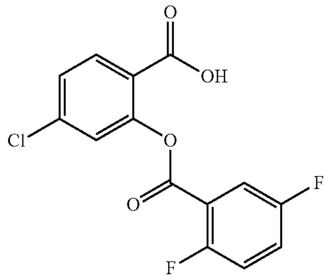

[Formula 3]

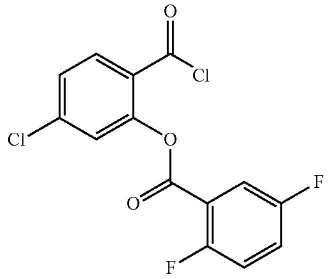

[Formula 4]

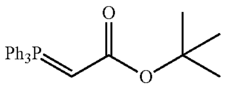

[Formula 5]

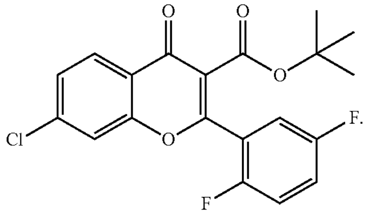

wherein the form IV crystal exhibits characteristic peaks at four or more diffraction angles 2θ±0.2° selected from the group consisting of 11.3, 14.7, 14.9, 16.9, 17.2, 22.5, and 25.7.

16. The method according to claim 14, wherein a temperature at which the compound of formula 1 is added to the methyl isobutyl ketone (MIBK) is 15 to 25° C.

* * * * *